US010458931B1

United States Patent
Richardson et al.

(10) Patent No.: US 10,458,931 B1
(45) Date of Patent: Oct. 29, 2019

(54) CONTACT IMAGING SENSOR HEAD FOR COMPUTED RADIOGRAPHY

(71) Applicant: Leidos, Inc., Reston, VA (US)

(72) Inventors: Rex David Richardson, Poway, CA (US); William L. Hicks, Escondido, CA (US); Mark Alan Peressini, San Diego, CA (US)

(73) Assignee: Leidos, Inc., Reston, VA (US)

(*) Notice: Subject to any disclaimer, the term of this patent is extended or adjusted under 35 U.S.C. 154(b) by 131 days.

(21) Appl. No.: 15/622,939

(22) Filed: Jun. 14, 2017

Related U.S. Application Data (60) Provisional application No. 62/351,390, filed on Jun. 17, 2016.

(51) Int. Cl.
*G01N 23/22* (2018.01)

(52) U.S. Cl.
CPC ....... *G01N 23/22* (2013.01); *G01N 2223/407* (2013.01); *G01N 2223/5015* (2013.01)

(58) Field of Classification Search
CPC .................................................. G01N 23/22
See application file for complete search history.

(56) References Cited

U.S. PATENT DOCUMENTS

| | | | |
|---|---|---|---|
| 4,582,988 A | 4/1986 | Aagano | 250/327.2 |
| 4,597,017 A | 6/1986 | Johnson et al. | 358/294 |
| 4,616,129 A | 10/1986 | Yamada et al. | 250/207 |
| 4,749,861 A | 6/1988 | Watanabe | 250/327.2 |
| 4,800,276 A | 1/1989 | Noguchi | 250/327.2 |
| 4,810,874 A | 3/1989 | Torii | 250/327.2 |
| 4,816,679 A * | 3/1989 | Sunagawa | H04N 1/0313 250/585 |
| 4,835,386 A | 5/1989 | Shimura et al. | 250/327.2 |
| 4,864,134 A | 9/1989 | Hosoi et al. | 250/327.2 |
| 4,883,961 A * | 11/1989 | Arakawa | G03B 42/02 250/584 |
| 4,931,642 A | 6/1990 | Hosoi et al. | 250/327.2 |
| 4,943,724 A | 7/1990 | Saotome et al. | 250/327.2 |
| 4,950,895 A | 8/1990 | Reinfelder | 250/327.2 |
| 4,954,706 A | 9/1990 | Takahashi et al. | 250/327.2 |
| 5,206,514 A | 4/1993 | Brandner et al. | 250/327.2 |
| 5,208,459 A * | 5/1993 | Morrone | H04N 1/00795 250/484.4 |
| 5,266,803 A | 11/1993 | Heffelfinger | 250/582 |
| 5,455,428 A | 10/1995 | Miyagawa | 250/586 |
| 5,483,081 A | 1/1996 | Hosoi | 250/585 |

(Continued)

FOREIGN PATENT DOCUMENTS

| | | | | |
|---|---|---|---|---|
| WO | WO 99/028765 | 6/1999 | | G01T 1/29 |
| WO | WO 02/003137 | 1/2002 | | G03B 42/02 |

*Primary Examiner* — David P Porta
*Assistant Examiner* — Djura Malevic
(74) *Attorney, Agent, or Firm* — Dawn-Marie Bey; Bey & Cotropia PLLC (57) ABSTRACT

A scan head design uses 1:1 (one-to-one) imaging microlens arrays to transfer the object plane X-ray image from a CR-plate onto a linear photosensor. The scan-head includes a housing having therein, an array of red light emitting diodes (LEDs), a red-absorbing filter, a microlens array, an infrared-filter, and a sensor. The housing faces the CR-plate and the scan-head is translated across the CR-plate to read out the X-ray image therein. The scan head is compact and provides for improved spatial resolution and reduced power requirements.

28 Claims, 5 Drawing Sheets

(56) References Cited

U.S. PATENT DOCUMENTS

| | | | | |
|---|---|---|---|---|
| 5,534,710 | A | 7/1996 | Suzuki | 250/588 |
| 5,608,774 | A | 3/1997 | Polichar et al. | 378/98.8 |
| 5,635,728 | A | 6/1997 | Cantu et al. | 250/584 |
| 5,654,556 | A | 8/1997 | Yasuda | 250/584 |
| 5,665,962 | A * | 9/1997 | Kimura | H04N 1/028 250/226 |
| 5,715,292 | A | 2/1998 | Sayag et al. | 378/98.8 |
| 5,864,362 | A | 1/1999 | Cutler | 348/96 |
| 6,052,432 | A | 4/2000 | Rieppo et al. | 378/98.2 |
| 6,140,663 | A * | 10/2000 | Neary | G03B 42/02 250/588 |
| 6,178,224 | B1 * | 1/2001 | Polichar | G01N 23/04 250/368 |
| 6,255,643 | B1 | 7/2001 | Sayag | 250/221 |
| 6,320,177 | B1 | 11/2001 | Sayag | 250/208.1 |
| 6,373,074 | B1 * | 4/2002 | Mueller | H04N 1/031 250/582 |
| 6,376,856 | B1 * | 4/2002 | Katagiri | G02B 26/10 250/584 |
| 6,555,838 | B1 * | 4/2003 | Livingston | G03B 42/02 250/584 |
| 6,642,535 | B2 * | 11/2003 | Gebele | G01T 1/2014 250/584 |
| 6,747,805 | B2 | 6/2004 | Sayag | 359/664 |
| 6,800,870 | B2 * | 10/2004 | Sayag | G11C 13/04 250/584 |
| 6,950,242 | B2 | 9/2005 | Sayag | 359/664 |
| 7,002,533 | B2 | 2/2006 | Sayag | 345/7 |
| 7,359,488 | B1 | 4/2008 | Sayag | 378/154 |
| 7,589,341 | B2 * | 9/2009 | Sayag | G11C 13/04 250/584 |
| 7,601,973 | B2 * | 10/2009 | Frankenberger | G01T 1/2012 250/484.4 |
| 7,825,394 | B2 * | 11/2010 | Sayag | G11C 13/04 250/227.23 |
| 7,929,220 | B2 | 4/2011 | Sayag | 359/738 |
| 9,099,333 | B2 * | 8/2015 | Imamura | H01L 25/0753 |
| 2001/0028047 | A1 * | 10/2001 | Isoda | G01T 1/2014 250/586 |
| 2001/0030303 | A1 * | 10/2001 | Ikami | G03B 42/02 250/584 |
| 2002/0033460 | A1 | 3/2002 | Nagli et al. | 250/583 |
| 2002/0158216 | A1 * | 10/2002 | Neriishi | G03B 42/08 250/584 |
| 2003/0179415 | A1 * | 9/2003 | Yasuda | G01T 1/2014 358/302 |
| 2004/0238765 | A1 * | 12/2004 | Bode | H04N 1/02815 250/584 |
| 2004/0238766 | A1 * | 12/2004 | Bode | G01T 1/2014 250/585 |
| 2006/0030738 | A1 * | 2/2006 | Vanmaele | G02B 5/223 568/9 |
| 2006/0180773 | A1 * | 8/2006 | Frankenberger | G01T 1/2014 250/484.4 |
| 2006/0180777 | A1 * | 8/2006 | Frankenberger | G01T 1/2014 250/584 |
| 2006/0180778 | A1 * | 8/2006 | Fasbender | G01T 1/2014 250/587 |
| 2006/0214123 | A1 * | 9/2006 | Liang | H04N 1/02815 250/584 |
| 2009/0173899 | A1 * | 7/2009 | Sayag | G11C 13/04 250/585 |
| 2015/0078520 | A1 * | 3/2015 | Watson | G01T 1/2014 378/62 |

* cited by examiner

CONTACT IMAGING SENSOR HEAD FOR COMPUTED RADIOGRAPHY

CROSS-REFERENCE TO RELATED APPLICATIONS

The present application claims benefit of priority to U.S. Provisional Patent Application No. 62/351,390, entitled "Contact Imaging Sensor Head for Computed Radiography," filed Jun. 17, 2016, the entirety of which is incorporated herein by reference.

FIELD OF THE EMBODIMENTS

The purpose of the invention is to provide an improved linear imaging sensor assembly which may be used as X-ray imaging diagnostics for military and first-responders working in explosive ordinance disposal (EOD) and improvised explosive device (IED) investigation and disposal.

BACKGROUND

Computed Radiography (CR) involves readout-scanning of a photostimulable storage phosphor plate (CR-plate) previously exposed to an X-ray source in an imaging mode. The technology was developed as an alternative to film-based radiography and has been used for decades in the medical and veterinary areas. The medical readout devices use flying-spot laser scanners with large and complex optical assemblies in bulky chassis designed for an office environment. These devices are not suitable for the man-portable, field applications intended for computed radiography products such as the Future Radiography System (FRS) and the Real Time Radiography (RTR) system products developed by Applicant, Leidos, Inc.

The Leidos FRS products are the only known CR systems compatible with field operations that also meet the form-factor requirements of the military and first-responder customers. The limiting form factors are the overall height (thickness) of the cassette/reader system, about 1.5 inch or less, plus the requirement for minimum dead space on two sides at a corner.

An existing Leidos product is based on a scan head described in U.S. Pat. No. 7,825,394 (hereafter the '394 Patent"), the substance of which is incorporated herein by reference in its entirety. The prior art scan head described in the referenced patent uses a linear array of charge-coupled device (CCD) photosensors placed very close to the CR plate to enable contact-transfer (sometimes referred to as proximity focusing) of the violet, stimulated light to the readout pixels. There are no imaging optics between the CR plate surface and the CCD array—only a thin filter and a protection film. The filter is required to eliminate the red stimulation light from the violet CR plate emission and is approximately 250 microns thick (est.). The protection film, typically 60-70 micron thick Mylar, protects the scan head, reduces damage to the fragile CR plate and provides a smooth-running interface. The total height of the head assembly is about 10 mm which is quite compact and helps meet the overall thickness goal. The width of the head is also about 10 mm although this dimension is less critical as long as the design supports the minimum dead-space requirement at one edge. The active length of the head is 14 inches with only a few mm of dead space on each end for coupling to the mechanical scan drive.

Red-light stimulation of the CR plate is accomplished using a dense array of LEDs aimed at the plate along the length of the prior art head. The LEDs are separated from the CCD array by a thin metal wall extending all the way down to the CR plate surface. This "knife-edge" interface results in thin line-source of red light that is created by scatter-diffusion through the 290 micron thick CR plate around to the region viewed by the CCD array. An advantage of this simple geometry is that the CCD array can be positioned directly against the knife-edge wall ensuring good alignment relative to the line-source emission. An additional advantage is that the flood-illuminated region directly under the LEDs affords effective erasure of the CR plate during the primary scan and also during the return-to-home of the head, if the LEDs remain energized. Obviously, the head can run the primary scan in only one direction.

The system runs in a pushbroom-style scan imaging mode taking about 25 seconds to travel the 17-inch length of the CR plate. The image is divided into square pixels 172 microns on a side. There are 2400 pixels in the 17-inch direction (direction of mechanical translation in FRS). Hence, the read-integration time for each pixel is about 10.5 ms. The LED power must be adjusted to bleach out more than 90% of the stored violet photons in this time interval, but not too high such that additional bleaching occurs outside the photosensitive collection region in the scan direction. Other than this requirement, the only limit on scan speed is the readout time of the CCD array and the capabilities of the mechanical drive system.

By way of example only, the CR plates are very high quality and may be supplied by a manufacturer such as Carestream Health, Inc. The CR plate is a highly diffusive granular phosphor material that is flat, smooth, and appears bright-white in room lights. The current FRS system uses the Carestream General Purpose or GP plate providing the highest X-ray stopping power.

SUMMARY OF THE EMBODIMENTS

In a first exemplary embodiment, a system for readout-scanning of a previously exposed photostimulable storage phosphor plate containing an X-ray image includes: a linear array of red light emitting diodes (LEDs) oriented at a predetermined angle to the exposed photostimulable storage phosphor plate to illuminate a gap-interface between the exposed photostimulable storage phosphor plate and a red-absorbing filter; and a microlens array for receiving image photons emitted from the exposed photostimulable storage phosphor plate responsive to the illumination from the linear array of red light emitting diodes (LEDs) and passed through the red-absorbing filter, wherein the microlens array forms the X-ray image on a linear sensor.

In a second exemplary embodiment, a scan-head for readout-scanning of a previously exposed photostimulable storage phosphor plate containing an X-ray image includes: a housing including therein, an array of red light emitting diodes (LEDs), a red-absorbing filter, a microlens array, an infrared-filter, and a sensor; a sheet of cover glass adhered to a first portion of a side of the housing facing the exposed photostimulable storage phosphor plate; and multiple pads adhered to at least a second and third portion of the side of the housing facing the exposed photostimulable storage phosphor plate; wherein the scan-head is translatable across the previously exposed photostimulable storage phosphor plate to read out the X-ray image therein.

In a third exemplary embodiment, subsystem for directing a read-out beam to a CR-plate to stimulate emission of image X-ray photons therefrom, includes: an array of red light emitting diodes (LEDs) for emitting read-out light; and a red-absorbing filter, wherein the array of red LEDs is oriented at a first predetermined angle to the CR-plate to illuminate a gap-interface between the CR-plate and a parallel side of the red-absorbing filter; and further wherein the red-absorbing filter includes a beveled edge facing in a direction of the linear array of red light emitting diodes (LEDs) and forming a second predetermined with a facing side of the CR-plate, such that the read-out beam and the beveled edge operate to produce the stimulated emission line-source of image X-ray photons.

BRIEF DESCRIPTION OF THE FIGURES

The following Figures are to be considered in conjunction with the detailed description below.

DESCRIPTION OF THE EMBODIMENTS

Figure 1A:
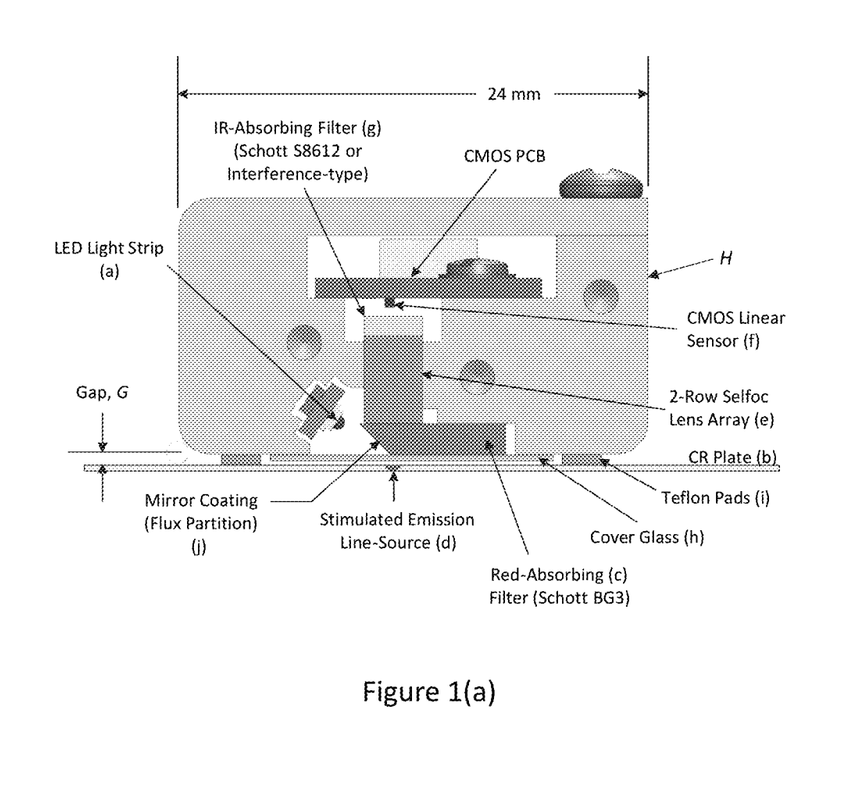
FIGS. 1(a) and 1(b) are cross-sectional, schematic views of a scan head design in accordance with a first embodiment described herein.
Figure 1B:
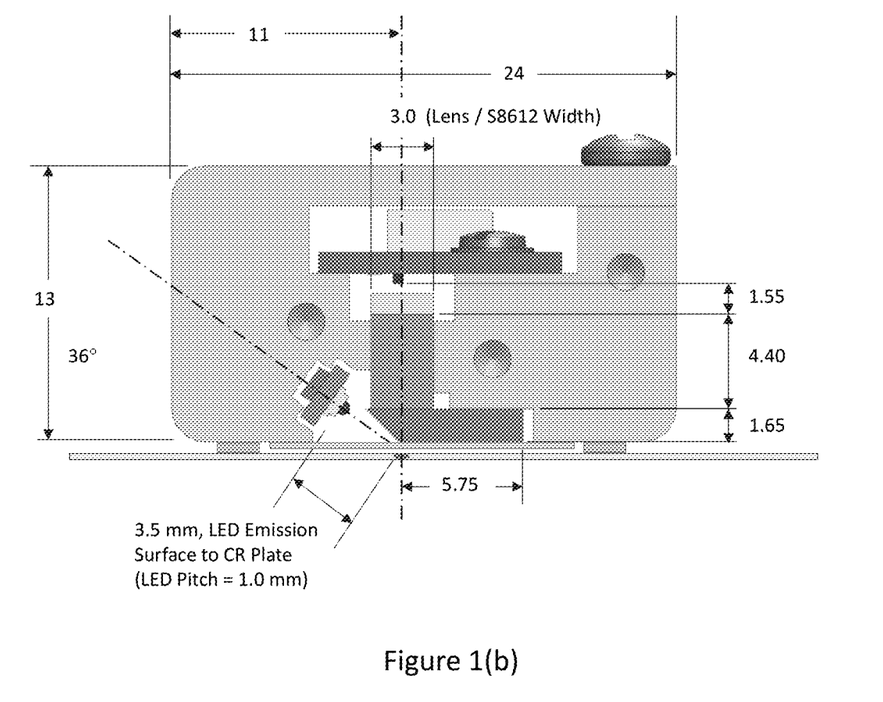

FIGS. 1(a) and 1(b) show a cross sectional view of a first embodiment of the present scan head design which uses 1:1 (one-to-one) imaging micro-lens arrays to transfer the object plane image onto a linear photosensor. This form of imaging should not be confused with proximity focusing as described above in the background.

The embodiment of FIGS. 1(a) and 1(b) consists of a red LED linear array or light strip (a) oriented to illuminate a gap-interface (G) between the CR plate (b) and a red-absorbing filter (c), e.g., Schott BG3, that passes the image photons emitted from the narrow line-source object (d) to a Selfoc Lens Array (SLA) (e) which forms the image at the CMOS linear sensor (f). In this exemplary embodiment an additional infrared-absorbing filter (g), e.g., Schott S182 or intereference-type filter, is used to eliminate the IR component of the LED light that leaks through the red-absorbing filter. A thin glass cover plate (h) bonded to the filter (c) and to the housing (H) seals the optics and CMOS sensor from moisture and contamination. Thin Teflon pads (i) elevate the scan head to prevent direct contact between the glass cover plate (h) and the CR plate (b). The pads (i) ensure smooth, low abrasion motion of the scan head while in contact with the CR plate. Positive pressure between the CR plate and the scan head is maintained by a spring and roller assembly incorporated into the cassette/reader design. The approximately 24 mm wide housing is representative of the prototype but the overall design can potentially be modified to be 18 mm to 20 mm in width.

In the embodiments herein, an exemplary baseline SLA is a model 20DG 2-row commercial off the shelf (COTS) product manufactured by GoFoton, a subsidiary of Nippon Sheet Glass, Inc. This lens array projects a 1:1 erect, real image onto the CMOS linear sensor. One skilled in the art recognizes that equivalent lens arrays are contemplated by this description and are considered to be within the scope of the embodiments.

The red-absorbing filter has a 45° angle-cut edge facing the LED array. The angle-cut is required to accommodate the ±25° acceptance angle of the 2-row SLA viewing the emission-line object and also directs the LED light across the interface gap. All distances and focusing properties of the system have been determined and optimized by 3-D optical raytrace modeling taking into account the emission spectrum and the dispersive/absorptive properties of the filters and lens material. These results show an optical spatial resolution of better than 6 lp/mm (line pairs per millimeter).

The surface of the beveled edge (j) is mirror-coated with aluminum or similar reflective metal to prevent the intense, direct LED light from entering the short-pass filter (c). All other optical pathways into the short-pass filter are blocked or sealed except for the front surface facing the CR plate. In the baseline embodiment, we have chosen thin-film aluminum applied by vacuum deposition. This choice provides the required isolation and also creates a mirror reflector that enhances the irradiation of the LED flood zone facilitating erasure of the CR plate. A less reflective coating, up to and including flat black, on the beveled edge surface (j) is also an option and may be selected to control the optical flux distribution. Thin metal shims may also be substituted for the coating.

The angle-cut, coated surface (j) acts as a baffle to cut off the LED light entering the gap between CR plate and the front surface of the red-absorbing filter (c) producing a sharp boundary in the red light impinging on the CR plate. The gap can be adjusted to provide an irradiated region on the CR plate surface with a width approximately equal to G/tan(θ), where G is the gap distance and B is the LED angle relative to the CR plate. We refer to this geometry as an "optical flux partition" describing the baffle-plus-gap functional geometry. Diffusion of red light from the LED flood zone into the gap region via bulk scattering in the CR plate is of secondary importance compared to this direct irradiation component.

The CR plate violet light emission in the band approximately 350 nm to 450 nm is stimulated by the irradiated region distributed over the CR plate. Approximately 0.3 mJ/cm$^2$ of incident red light (nominal center wavelength of 600 nm) is required to liberate about 95% of the stored violet light representing the X-ray image. The LED flux is accumulated during an integration time determined by the push-broom-scan time needed to form square pixels in the digital image. In the prior art FRS product and in the present embodiment, that integration time is approximately 10 ms. Very intense LED light sources are required to provide irradiation 0.3 mJ/cm$^2$ in 10 ms while maintaining a high degree of uniformity.

This level of irradiation can be best achieved in our geometry using a high-density (high number per unit length) linear LED array placed a few millimeters from the CR plate/gap interface. The red-light intensity at the interface is further increased by selecting surface-mount LED devices having small, dome lenses that focus the light in the forward direction. The embodied design is based on placing these LEDs at a spacing (pitch) of approximately 1.0 mm. The geometry is shown in FIGS. 1(a) and 1(b). We have determined, through ray trace simulations and direct measurements, that this LED array can deliver the required irradiation operating at about 40% of its maximum power. The intensity uniformity at the gap interface is better than two percent as predicted by ray tracing results and by direct measurements in the laboratory.

Figure 2:
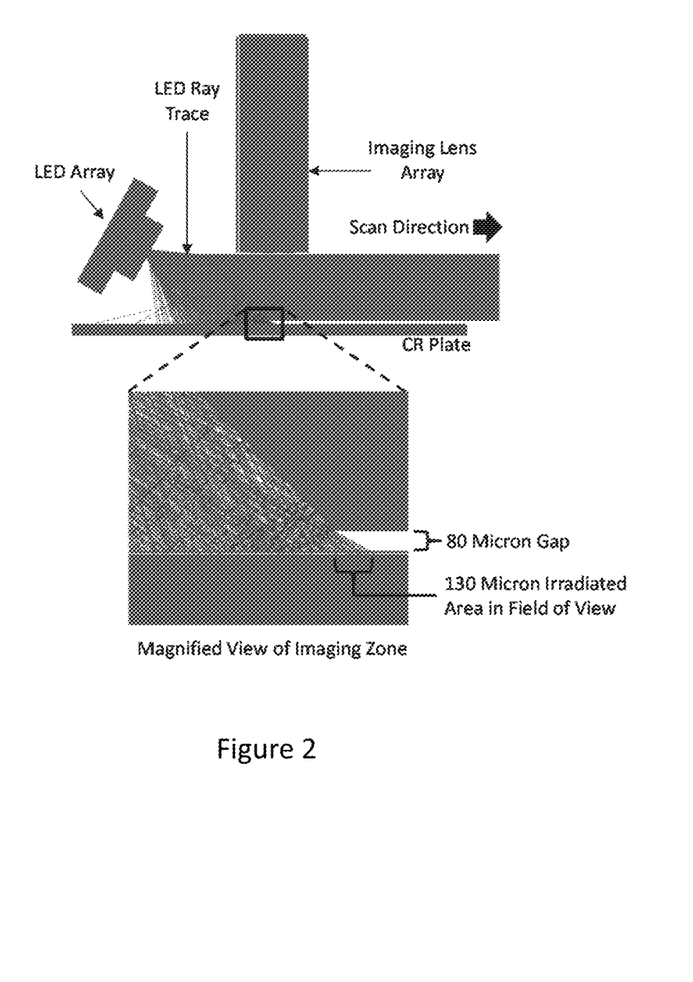
FIG. 2 is an illumination geometry as modeled with ray tracing.

FIG. 2 shows an example of the illumination geometry as modeled in our ray tracing simulations. Our optical ray tracing simulations are carried out using the commercial engineering code TracePro® sold by Lambda Research, Inc. TracePro provides advanced tools for analysis of imaging systems and lighting conditions including utilities for exact modeling of LED components based on vendor data specifications. In this case we show the results for an 80 micron air gap (G) that produces a surface irradiation pattern approximately 130 microns in width. The gap width (G) can be adjusted larger or smaller in the final design. As in the prior art FRS design, image scanning must be unidirectional. By inspection one can see that most of the LED emission impinges on the CR plate downstream of the imaging interface providing for robust erasure of plate in the scan direction and in the return of the scan head to the home position (assuming the LED array remains energized).

Form Factor

From FIG. 1(b), it is clear that this embodiment of the invention meets the requirement for a scan head height, i.e., 13 mm, that fits within a 1.5" cassette (or approximately 38 mm). One skilled in the art recognizes that the present embodiment can be modified to accommodate lengths of 8"-17" across the full range of anticipated scanner product dimensions.

Operational Characteristics

Various COTS components may be incorporated in the embodiments in accordance with required environmental extremes and are expected to outperform the prior art systems in this respect. This includes the SLA and CMOS array. The optical design has been developed to meet expected environmental and ruggedness requirements. The LED illumination system has been selected to enable pixel-integration times of less than 10 ms so as to maintain read times of less than 30 seconds. The LED array is much more efficient at stimulating blue emission and therefore requires only about one third the electrical power compared to the LED array in the prior art scan head.

Readout electronics for CMOS line scanners are much simpler than for CCDs since the charge-shifting and transimpedance amplification is all taken care of on the silicon adjacent to the photodiode pixel. All that is needed is a clock, a frame start-pulse (determines the integration time) and an A/D converter. There are various design options for forming and reading out the image data but the board-level computer currently required in the prior-art FRS can be eliminated, reducing cost, lowering the power draw and freeing up space behind the CR plate bed. The extra space will enable a new cassette design having a thickness less than the current 1.5".

Higher Performance

Figure 3A:
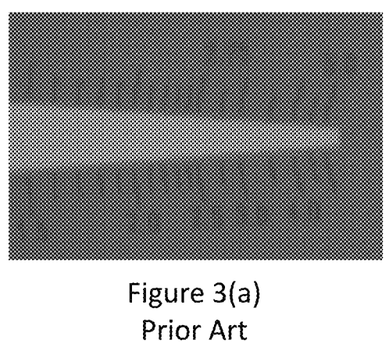
FIG. 3(a) is an images of line pair gauges from the prior art.
Figure 3B:
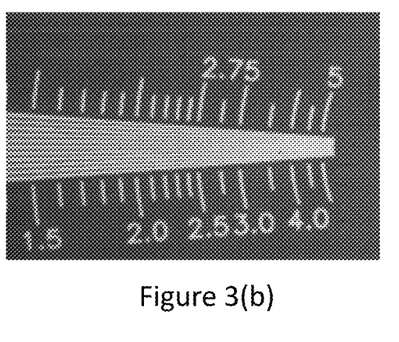
FIG. 3(b) is an images of line pair gauges from the first embodiment described herein.

Spatial resolution in the proximity-focus design of the prior art head is limited by the approximately 350 micron separation distance between the CR plate and CCD array. The prior art system has a spatial resolution of less than 2 lp/mm, on average. The embodiment described and illustrated herein has an optical resolution better than 6 lp/mm. Spatial resolution is primarily limited by the CR plate characteristics and pixel size. In a first exemplary embodiment using 125 micron pixels a spatial resolution of approximately of 2.75-3.0 lp/mm in all orientations has been achieved. We have verified this result in prototype testing using the standard Carestream GP plate. Even higher resolution is possible with thinner CR plates and custom pixel sizes. FIGS. 3(a) and 3(b) present images of line pair gauges from the prior art system (FIG. 3(a)) and from the exemplary embodiment (FIG. 3(b))—taken at equivalent scan speeds. The prior art FRS image in FIG. 3(a) illustrates the worst-case orientation: in the direction of the sensor. Clearly the spatial resolution is no better than about 1.6 lp/mm in this case. The spatial resolution example from the exemplary embodiment FIG. 3(b) was obtained under realistic operating conditions.

Figure 4:
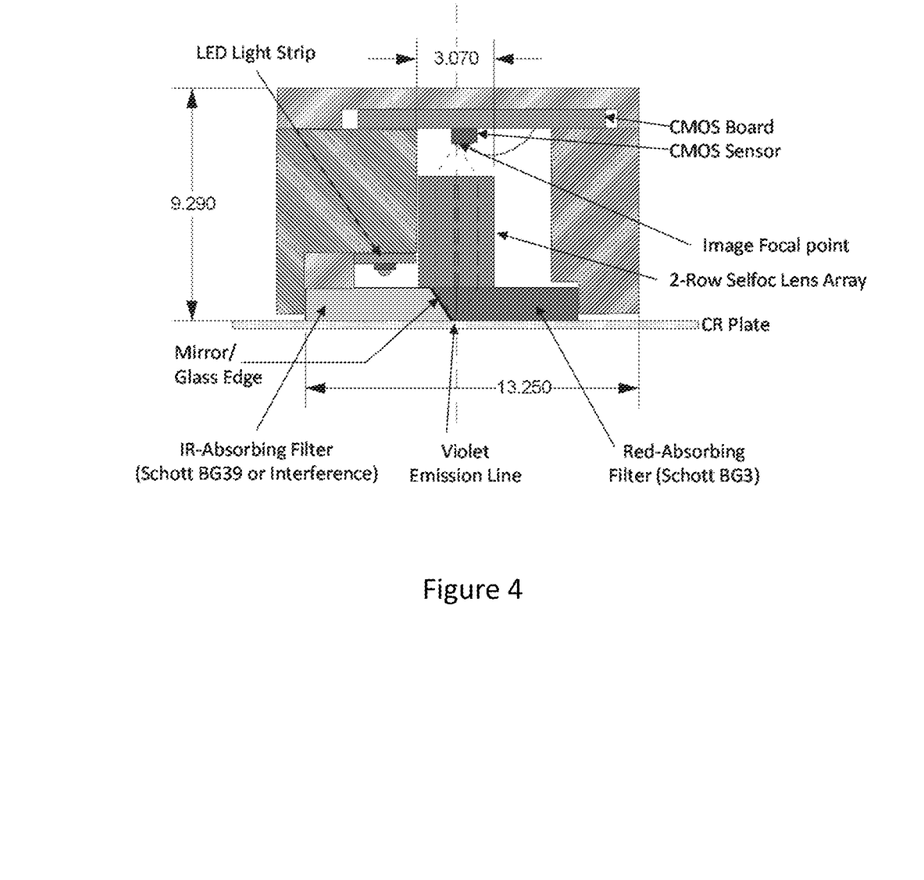
FIG. 4 is a cross-sectional, schematic view of a scan head design in accordance with a second embodiment described herein.

In a second embodiment shown in FIG. 4, the CR plate is viewed by a 2-row Selfoc Lens Array (SLA) projecting a 1:1 erect real image onto a CMOS linear sensor. At the interface of the SLA and the CR is an infrared (IR) filter with a beveled edge having a thick (500 nm) aluminized coating coupled to a blue/violet short pass filter on the opposite side with a mating bevel. The mirrored surface directs LED light from a red LED array onto the CR plate at precisely the centerline of the SLA field of view. This glass/mirror edge defines a line source on the CR plate by way of diffusion of the red light through the 290 micron thick phosphor matrix across the edge-tip into the field of view of the SLA. The emission of violet light (350-450 nm) overlays the resulting red light line-source as distributed in the CR plate. Approximately 0.3 mJ/cm$^2$ of red light (550-650 nm) is required to liberate 95% of the stored violet light representing the X-ray image.

Measurements indicate the half-width of the glass/mirror line source to be on the order of 75 microns. Using a single row CMOS photosensor array (1×N pixels) dictates that the pixel size be larger than the line source to provide efficient collection of the violet light. We have developed a custom CMOS array having 125 micron wide by 200 micron long pixels. The 200 micron length, exceeding the full width of the imaged line source, is intended to facilitate final alignment of the optical system while minimizing loss of signal and maintaining full spatial resolution in all orientations. The fill factor, dark current, read noise and sensitivity parameters of the custom CMOS device were selected to achieve the signal-to-noise goals of the operating system which will equal or exceed that of the prior art system.

The glass/mirror optical flux partition and filter combination interface of the embodiments is superior to the plastic tape, metal wall and epoxy/dye-filter interface of the prior art scan head. Fabricated using optical CNC (computer numerical control) technology, this embodiment provides extremely precise (e.g., ±55 micron) alignment of the violet line-source emission with the optical axis of the SLA over the full length of the scan head. The embodiment described herein stimulates the CR plate emission via direct illumination controlled by the flux partition, LED and gap geometry, whereas the prior art design relies upon diffusion of the red LED light through the CR plate bulk material past the metal-foil knife edge. Since diffusion is a second order effect compared to the direct surface illumination, the present embodiments are able to operate at about one third the LED power of the prior art scan head.

The foregoing discussion discloses and describes merely exemplary embodiments of the technology described herein. One skilled in the art will readily recognize from such discussion and from the accompanying drawings that various changes, modifications and variations can be made therein without departing from the spirit and scope of the invention.

The invention claimed is:

1. A system for readout-scanning of a previously exposed photostimulable storage phosphor plate containing an X-ray image comprising:
    a linear array of red light emitting diodes (LEDs) oriented at a predetermined angle to the exposed photostimulable storage phosphor plate to illuminate directly both a gap-interface between the exposed photostimulable storage phosphor plate and a red-absorbing filter and a first predetermined portion of the exposed photostimulable storage phosphor plate; and a microlens array for receiving image photons emitted from the exposed first predetermined portion of the photostimulable storage phosphor plate responsive to the illumination from the linear array of red light emitting diodes (LEDs) and passed through the red-absorbing filter, wherein the microlens array forms the X-ray image on a linear sensor.

2. The system of claim 1, further comprising: an IR filter located between the microlens array and the linear sensor.

3. The system of claim 1, wherein the predetermined angle is less than 45 degrees.

4. The system of claim 1, wherein the red-absorbing filter includes a beveled edge facing in a direction of the linear array of red light emitting diodes (LEDs).

5. The system of claim 4, wherein the beveled edge of the red-absorbing filter includes a reflective coating.

6. The system of claim 1, wherein the linear sensor is a CMOS sensor.

7. The system of claim 1, wherein the microlens array is a 2-row Selfoc lens array.

8. The system of claim 1, wherein the system height is equal to or less than 13 mm.

9. The system of claim 1, wherein the linear array of red light emitting diodes (LEDs) comprises surface-mount LED devices with individual dome lenses for focusing LED emitted light in a forward direction.

10. The system of claim 9, wherein the LEDs have a spacing of approximately 1.0 mm.

11. The system of claim 9, wherein the system focuses the LED emitted light at a line on the exposed photostimulable storage phosphor plate resulting in a stimulated emission line-source of image photons therefrom.

12. A scan-head for readout-scanning of a previously exposed photostimulable storage phosphor plate containing an X-ray image comprising:
    a housing including therein,
        a linear array of red light emitting diodes (LEDs),
        a red-absorbing filter,
        a microlens array,
        an infrared-filter, and
        a sensor;
        wherein the linear array of red light emitting diodes is oriented at a predetermined angle to the exposed photostimulable storage phosphor plate to illuminate directly a first predetermined portion of the exposed photostimulable storage phosphor plate; and
        further wherein the microlens array receives image photons emitted from the exposed first predetermined portion of the photostimulable storage phosphor plate responsive to the illumination from the linear array of red light emitting diodes (LEDs) after passing through the red-absorbing filter, and forms the X-ray image on the sensor from at least the first predetermined portion of the exposed photostimulable storage phosphor plate;
    a sheet of cover glass adhered to a first portion of a side of the housing facing the exposed photostimulable storage phosphor plate; and
    multiple pads adhered to at least a second and third portion of the side of the housing facing the exposed photostimulable storage phosphor plate;
    wherein the scan-head is translatable across the previously exposed photostimulable storage phosphor plate to read out the X-ray image therein.

13. The scan-head according to claim 12, wherein the housing has dimensions equal to or less than a height of 13 mm and a width of 24 mm.

14. The scan-head of claim 12, wherein the array of red LEDs illuminates a gap-interface between the exposed photostimulable storage phosphor plate and the red-absorbing filter.

15. The scan-head of claim 14, wherein the predetermined angle is less than 45 degrees.

16. The scan-head of claim 12, wherein the red-absorbing filter includes a beveled edge facing in a direction of the linear array of red light emitting diodes.

17. The scan-head of claim 16, wherein the beveled edge of the red-absorbing filter includes a reflective coating.

18. The scan-head of claim 12, wherein the sensor is a linear CMOS sensor.

19. The scan-head of claim 12, wherein the microlens array is a 2-row Selfoc lens array.

20. The scan-head of claim 12, wherein the array of red light emitting diodes comprises surface-mount LED devices with individual dome lenses for focusing LED emitted light in a forward direction.

21. The scan-head of claim 20, wherein the LEDs have a spacing of approximately 1.0 mm.

22. The scan-head of claim 20, wherein the scan-head focuses the LED emitted light at a line on the exposed photostimulable storage phosphor plate resulting in a stimulated emission line-source of image photons therefrom.

23. A subsystem for directing a read-out beam to a CR-plate to stimulate emission of image X-ray photons therefrom, comprising:
    an array of red light emitting diodes (LEDs) for emitting read-out light; and
    a red-absorbing filter,
    wherein the array of red LEDs is oriented at a first predetermined angle to the CR-plate to illuminate a gap-interface between the CR-plate and a parallel side of the red-absorbing filter; and
    further wherein the red-absorbing filter includes a beveled edge facing in a direction of the linear array of red light emitting diodes (LEDs) and forming a second predetermined angle with a facing side of the CR-plate, such that the read-out beam and the beveled edge operate to direct the read-out beam to a first predetermine portion of the CR-plate and produce the stimulated emission line-source of image X-ray photons from the first predetermined portion of the CR-plate for receipt thereof by a sensor.

24. The subsystem of claim 23, wherein the first predetermined angle is less than 45 degrees.

25. The subsystem of claim 23, wherein the second predetermined angle is approximately 45 degrees.

26. The subsystem of claim 23, wherein the beveled edge of the red-absorbing filter includes a reflective coating.

27. The subsystem of claim 23, wherein the array of red light emitting diodes (LEDs) comprises surface-mount LED devices with individual dome lenses for focusing LED emitted light in a forward direction.

28. The subsystem of claim 27, wherein the LEDs have a spacing of approximately 1.0 mm.

* * * * *